United States Patent [19]

Ginnaga et al.

[11] Patent Number: 4,563,303

[45] Date of Patent: Jan. 7, 1986

[54] METHOD FOR PURIFICATION OF FILAMENTOUS HEMAGGLUTININ

[75] Inventors: Akihiro Ginnaga; Shin Sakuma; Tsukasa Nishihara; Tomitaka Tashiro; Sadao Susumi; Tetsuo Kawahara; Hiroshi Mizokami, all of Kumamoto, Japan

[73] Assignee: Judicial Foundation The Chemosero-Therapeutic Research Institute, Kumamoto, Japan

[21] Appl. No.: 722,381

[22] Filed: Apr. 12, 1985

[30] Foreign Application Priority Data

| | | | |
|---|---|---|---|
| Apr. 14, 1984 | [JP] | Japan | 59-075314 |
| Apr. 25, 1984 | [JP] | Japan | 59-084778 |
| May 7, 1984 | [JP] | Japan | 59-091631 |

[51] Int. Cl.⁴ ........ C07G 7/00; A61K 39/10

[52] U.S. Cl. ........ 260/112 R; 424/92; 435/822

[58] Field of Search ........ 260/112 R; 424/92; 435/822

[56] References Cited

U.S. PATENT DOCUMENTS

| | | | |
|---|---|---|---|
| 3,842,061 | 10/1974 | Andersson et al. | 260/112 B |
| 3,920,625 | 11/1975 | Andersson et al. | 260/112 B |
| 4,138,287 | 2/1979 | Andersson et al. | 424/89 X |
| 4,168,300 | 9/1979 | Andersson et al. | 260/112 R X |
| 4,195,076 | 3/1980 | Fontanges | 424/89 X |
| 4,247,452 | 1/1981 | Irons et al. | 260/112 R |
| 4,247,539 | 1/1981 | Iritani et al. | 424/92 |
| 4,455,297 | 6/1984 | Syukuda et al. | 424/92 |
| 4,515,714 | 5/1985 | Kawahara et al. | 260/112 R |

FOREIGN PATENT DOCUMENTS

| | | | |
|---|---|---|---|
| 0121249 | 10/1984 | European Pat. Off. | 424/92 |

OTHER PUBLICATIONS

Inf. Immun., 9, 801–810 (1974), Sato et al.
Inf. Immun., 25, 460–462 (1979), Arai et al.
Inf. Immun., 31, 1223–1231 (1981), Sato et al.
Inf. Immun., 32, 243–250 (1981), Munoz et al.
Biochimica et Biophysica Acta, 659, 7–14 (1981), Turner et al.

*Primary Examiner*—Howard E. Schain
*Attorney, Agent, or Firm*—Wegner & Bretschneider

[57] ABSTRACT

Improved method for the purification of filamentous hemagglutinin (F-HA) on industrial scale which comprises contacting a culture of a microorganism of the genus Bordetella with a cellulose sulfate gel, a polysaccharide gel chemically bound with dextran sulfate, or a crosslinked polysaccharide sulfate gel, thereby adsorbing F-HA on the gel, and then eluting F-HA from the gel. Said method can give a highly purified F-HA which does not contain any other proteins, lipid, saccharides, etc. and further undesirable endotoxin, and hence can be used for producing various reagents, medicines and pertussis vaccine.

12 Claims, No Drawings

METHOD FOR PURIFICATION OF FILAMENTOUS HEMAGGLUTININ

The present invention relates to an improved method for the purification of filamentous hemagglutinin (hereinafter, referred to as "F-HA"). More particularly, it relates to a method for preparing a highly purified F-HA by contacting a culture of a microorganism of the genus Bordetella with a cellulose sulfate gel, a polysaccharide gel chemically bound with dextran sulfate, or a crosslinked polysaccharide sulfate gel, thereby adsorbing F-HA on the gel, and then eluting F-HA from the gel.

TECHNICAL FIELD

Microorganisms of the genus Bordetella include *Bordetella pertussis, Bordetella parapertussis, Bordetella bronchiseptica* which produce various biologically active substances. The F-HA is one of these biologically active substances, and any microorganism of the genus Bordetella can produce F-HA.

It has recently been noticed that F-HA shows an important function in the prophylaxis of infection of *B. pertussis* and infectious disease thereof and hence is useful as an antigen for prophylaxis of infection of *B. pertussis* [cf. Sato, Y. et al.; Infect. Immun., 31, 1223–1231 (1981), and Seminars in Infectious Diseases IV, Bacterial Vaccine, 380–385 (1982)]. Besides, it has been confirmed that all F-HA produced by various microorganisms of the genus Bordetella are not different immunologically [cf. Arai, H. et al.; Infect. Immun., 32, (1), 243–250 (1981)], and hence, each F-HA may be commonly useful as a component for vaccines effective against all microorgnisms of the genus Bordetella. From these viewpoints, it has been desired to develop an improved method for the separation and purification of the biologically active F-HA on industrial scale.

PRIOR ART

It is known that F-HA can be isolated and purified by subjecting the supernatant of *B. pertussis* culture to fractionation with ammonium sulfate, subjecting the resultant to a sucrose density gradient centrifugation, followed by gel filtration twice [cf. Sato, Y. et al.; Infect. Immun., 9, 801 (1974)]. However, this method requires a plenty of steps and hence is very complicated, and further gives the desired F-HA only in a low yield, and hence, this method can not be used on industrial scale.

It is also known to purify *B. pertussis* F-HA by an ion exchange chromatography and a gel filtration [cf. Arai, H. et al.; Infect. Immun., 25, 460 (1979)]. However, according to this method, the desired F-HA is obtained only in a low yield, and further, it is very difficult to remove undesirable *B. pertussis* endotoxin, and hence, this method can not practically be used, either.

Other known methods are a combination of hydroxyapatite adsorption chromatography, haptoglobin affinity chromatography, ammonium sulfate fractionation, and gel filtration [cf. Cowell, J. L. et al.; Seminars in Infectious Diseases IV, Bacterial Vaccine, 37, 1 (1982)], and a combination of hydroxyapatite adsorption chromatography, specific antibody-affinity chromatography, and sucrose density gradient ultracentrifugation [cf. Watanabe et al.; J. of Bacteriology Japan, 38, 423 (1983)]. However, these methods requires a plenty of steps and hence is complicated, and further, the F-HA is obtained only in a low yield. Besides, the used hydroxyapatite is very expensive, and the gel for affinity chromatography is not commercially available and is hardly obtainable, and the materials for the gel are also expensive. From these many drawbacks, the above methods are not suitable for producing F-HA on industrial scale.

OBJECT OF INVENTION

The present inventors have extensively studied on an improved method for the separation and purification of F-HA on industrial scale, and have found that the desired highly purified F-HA can be obtained by contacting a culture of microorganisms of the genus Bordetella with a cellulose sulfate gel, a polysaccharide gel chemically bound with dextran sulfate, or a crosslinked polysaccharide sulfate gel, thereby adsorbing F-HA on the gel and separating out any undesirable contaminants, and then eluting F-HA from the gel.

Thus, an object of the present invention is to provide a simple and industrial method for the purification of F-HA which is biologically active and is useful in a medical field. Another object of the invention is to provide a method for producing a highly purified F-HA which is useful as a component for vaccine against Bordetella microorganisms. These and other objects and advantages of the present invention will be apparent to skilled persons from the following decription.

SUMMARY OF INVENTION

The method for the purification of F-HA of the present invention comprises the steps of treating a culture of a microorganism of the genus Bordetella with a cellulose sulfate gel, a polysaccharide gel chemically bound with dextran sulfate, or a crosslinked polysaccharide sulfate gel, thereby adsorbing F-HA on the gel, and then eluting F-HA from the gel.

DETAILED DESCRIPTION OF INVENTION

The starting culture of a microorganism of the genus Bordetella includes cultures of microorganisms of the genus Bordetella, such as *Bordetella pertussis, Bordetella parapertussis, Bordetella bronchiseptica.* Preferable culture is a culture of *Bordetella pertussis* which is produced as follows:

That is, *B. pertussis* is cultured in a conventional medium, such as Cohen-Wheeler medium or Stainer-Scholte medium, in a usual manner, such as stationary culture, shake culture, or spinner culture (this is synonym of shaking culture, aeration culture, and aeration spinner culture). The culture broth is used in the present invention after being subjected to centrifugation to remove the cells, or after being fractured, followed by centrifugation, or after being partially purified by conventional purification methods. According to the present invention, the supernatant of culture can be applied to as it stands, that is, the previous purification, such as salting out, extraction, ultracentrifugation, etc. is not necessarily applied, but the supernatant can be directly subjected to chromatography with cellulose sulfate gel, a polysaccharide gel chemically bound with dextran sulfate, or a crosslinked polysaccharide sulfate gel, and hence, the purification can be done in a simple step.

The sulfuric acid ester of cellulose used as the cellulose sulfate gel in the present invention is obtained by sulfating a cellulose, preferably a crystalline cellulose or cellulose having crystalline area and non-crystalline area. The sulfuric acid ester of cellulose thus obtained retains well the original shape (preferably spherical shape) of the starting material and is insoluble in an aqueous medium and has excellent physical stability, and hence, is suitable as a gel of chromatography. These starting celluloses are commercially available, for example, Abicel (manufactured by Asahi Chemical, Japan), Cellulofine GC-15, GH-25, GC-100, or GC-200 (manufactured by Chisso Corp., Japan). The sulfation of the cellulose can be carried out by a conventional method, for example, by treating a gel of cellulose with chlorosulfonic acid, anhydrous sulfuric acid, or other sulfating agent in an organic solvent (e.g. pyridine).

The polysaccharide gel chemically bound with dextran sulfate is produced by chemically binding a dextran sulfate to a polysaccharide gel derivative. Various products of the dextran sulfate are commercially available, among which the products used usually for biological purposes are preferably used. The polysaccharide gel derivative includes gel derivatives which are prepared by subjecting a polysaccharide (e.g. agarose, dextran, cellulose, etc.) to conventional treatments for giving properties suitable for using as a carrier for chromatography, such as crystallization purification treatment, three-dimensional crosslinking, molding, etc. These products are also commercially available and include, for example, an agarose gel such as Sepharose (manufactured by Pharmacia, Sweden), a dextran gel such as Sephadex (manufactured by Pharmacia, Sweden), a cellulose gel such as Abicel (manufactured by Asahi Chemical, Japan). The chemical binding of the dextran sulfate and the polysaccharide can be done by various methods, for example, by a method of Andersone et al. using cyanobromide (cf. Japanese Patent First Publication No. 114018/1977), or a method using cyanobromide and also lysine (as a spacer) [cf. Bryan M. Turner et al.; Biochimica et Biophysica Acta, 659, 7–14 (1981)]. One product of dextran sulfate-agarose gel is already on the market, for example, dextran sulfate-Sepharose CL 4B (manufactured by Pharmacia, Sweden).

The sulfuric acid ester of a crosslinked polysaccharide includes a sulfuric acid ester of polysaccharides, such as dextran, cellulose, agarose, which is crosslinked with a crosslinking agent, such as epichlorohydrin, dichlorohydrin, dibromohydrin, ethylene glycol bisepoxypropyl ether. The crosslinked polysaccharides are commercially available, for example, crosslinked dextrans such as Sephadex G-10, G-25, G-50, and G-100 (manufactured by Pharmacia, Sweden), crosslinked agaroses such as Sepharose CL-2B, CL-4B, and CL-6B (manufactured by Pharmacia, Sweden), and crosslinked celluloses such as Cellulofine GCL-25, GCL-90 (manufactured by Chisso Corp., Japan). The sulfation of the crosslinked polysaccharide can be carried out by a conventional method, for example, by treating a gel of the crosslinked polysaccharide with chlorosulfonic acid, anhydrous sulfuric acid, or other sulfating agent in an organic solvent (e.g. pyridine).

The isolation and purification of F-HA from a culture of microorganisms of the genus Bordetella, e.g. *B. pertussis* with these gels are carried out in the following manner.

The cellulose sulfate gel, dextran sulfate-polysaccharide gel and crosslinked polysaccharide sulfate gel are previously equilibrated with an appropriate buffer having a neutral pH (e.g. pH 6–9), a specific conductivity of about 5 to 25 ms/cm, such as 0.2M sodium chloride-added 0.01M phosphase buffer, and then used for adsorption of F-HA.

The purification treatments such as adsorption of F-HA onto the cellulose sulfate gel or other gels, washing of the gels adsorbing the F-HA and elution of the F-HA can be carried out by a conventional industrially employed operation such as batch method or column method. In case of batch method, the cellulose sulfate gel or other gels are added to a culture supernatant of *B. pertussis,* and the mixture is gently stirred at pH 6.0–9.0, at a temperature of 0°–30° C. for 10 to 60 minutes, whereby F-HA is adsorbed onto the gels. The culture of *B. pertussis* used in the above method is usually regulated to a specific conductivity in the range of 5.0 to 25.0 ms/cm by concentrating or diluting it.

After completion of adsorption, the culture-gel mixture is added onto a filter, and the gel is separated from the filtrate by suction. The separated gel is washed by suction with an appropriate buffer having a specific conductivity of about 5 to 25 ms/m and a pH of about 5.0 to 10.0, for example, 0.2M sodium chloride-added 0.02M McIlvaine's buffer, 0.3M sodium chloride-added 0.01M phosphate buffer, or 0.3M sodium chloride-added 0.01M Tris-HCl buffer, etc. Thereafter, the adsorbed F-HA is eluted with an appropriate buffer having a pH of about 5.0 to 10.0 and a specific conductivity of about 25 to 130 ms/cm (larger specific conductivity than that of the above buffer for washing), such as, for example, 1.5M sodium chloride-added McIlvaine's buffer, 1.5M sodium chloride-added phosphate buffer, etc.

In case of column method, the starting solution to be treated, the buffer for washing and the buffer for elution are the same as those used in the batch method as mentioned above. The speed of passing the solution is controlled in the range of about 10 ml/cm$^2$/hour to 500 ml/cm$^2$/hour.

According to the above purification method, the F-HA in the culture supernatant of *B. pertussis* is specifically remarkably adsorbed, and hence, the purification degree of F-HA becomes several ten folds and further the recovery rate of F-HA reaches to from more than 90% to almost 100%. Beside, the purified F-HA has so high specific activity as $0.9–1.5\times10^5$ F-HA-Ab-ELISA unit/mg protein [measured by F-HA.ELISA method, cf. Sato, Y. et al.; Infect. Immun., 41, 313–320 (1983)], and further, forms a single band in a polyacrylamide disc electrophoresis analysis (pH 4.5). Moreover, *B. pertussis* endotoxin is almost completely removed to the level which is available to use as vaccine.

According to the above purification method, the desired F-HA can be isolated from the starting culture of *B. pertussis* in a high yield and high purity with very simple operation. Besides, the chromatography adsorbent can be prepared in a low cost and also can be used repeatedly without degradation. Accordingly, the method is excellent from economical viewpoint. Thus, the above purification method is very excellent as an industrial method for production of a highly purified F-HA. If necessary, the purification may be combined with conventional purification methods, such as sucrose density gradient ultracentrifugation, ion exchange chromatography, etc.

The purified F-HA thus obtained is very pure and does not contain any other proteins, lipid, saccharides, etc. and further undesirable endotoxin, and hence can be used for producing various reagents, medicines and pertussis vaccine.

The present invention is illustrated by the following Preparations and Examples, but should not be construed to be limited thereto.

PREPARATION 1

To pyridine (600 ml) is added dropwise chlorosulfonic acid (117 g) at below 0° C. After the addition, the mixture is heated to 65°-70° C. To the mixture is added crystalline cellulose gel (Cellulofine GC-15, manufactured by Chisso Corp.) (80 g), and the mixture is stirred at 65°-70° C. for 3 hours. After the reaction, the reaction mixture is cooled and neutralized with 10% aqueous sodium hydroxide. The gel thus obtained is separated by filtration and washed well with 0.01M phosphate buffer-aqueous sodium chloride mixture to give a cellulose sulfate gel.

PREPARATION 2

To pyridine (600 ml) is added dropwise chlorosulfonic acid (117 g) at below 0° C. After the addition, the mixture is heated to 65°-70° C. To the mixture is added crystalline cellulose (Abicel for chromatography, manufactured by Asahi Chemical, Japan) (80 g), and the mixture is stirred at 65°-70° C. for 4 hours. After the reaction, the reaction mixture is cooled and then neutralized with 10% aqueous sodium hydroxide. The gel thus obtained is separated by filtration and washed well with 0.01M phosphate buffer-aqueous sodium chloride mixture to give a cellulose sulfate gel.

PREPARATION 3

To pyridine (500 ml) is added dropwise chlorosulfonic acid (82 g) at 0°-5° C. After the addition, the mixture is heated to 65°-70° C. To the mixture is added crystalline cellulose gel (Cellulofine GH-25, manufactured by Chisso Corp.) (80 g), and the mixture is stirred at 65°-70° C. for 4 hours. After the reaction, the reaction mixture is cooled and then neutralized by gradually adding thereto 10% aqueous sodium hydroxide. The gel thus obtained is separated by filtration and washed well with 0.01M phosphate buffer-aqueous sodium chloride mixture (pH 7.2) to give a cellulose sulfate gel.

PREPARATION 4

Sodium dextran sulfate (5 g) is dissolved in 0.5M aqueous sodium carbonate (200 ml), and thereto is added Sepharose CL-4B (agarose gel, manufactured by Pharmacia, Sweden) (20 ml) which is equilibrated by 0.5M aqueous sodium carbonate, and the mixture is gently stirred. To the mixture is added with stirring a solution of cyano bromide (10 g) in distilled water (100 ml). The mixture is maintained for 15 minutes while keeping at pH 11 by adding 5M aqueous sodium hydroxide. Thereafter, the mixture is stirred at room temperature for 17 hours, while allowing to lower the pH value. After the reaction, the reaction mixture is filtered with a glass filter, and the gel thus obtained is washed well with 0.15M sodium chloride-added phosphate buffer (pH 7.2) to give dextran sulfate agarose gel (20 ml).

PREPARATION 5

To pyridine (200 ml) is added dropwise chlorosulfonic acid (11 ml) at below 0° C. After the addition, the mixture is heated to 65°-70° C. To the mixture is added epichlorohydrin-crosslinked dextran (Sephadex G-50, manufactured by Pharmacia, Sweden) (7.5 g), and the mixture is stirred at 65°-70° C. for 4 hours. After the reaction, the reaction mixture is cooled and then neutralized with aqueous sodium hydroxide. The gel thus obtained is separated by filtration and washed well with 0.01M phosphate buffered saline solution to give a crosslinked dextran sulfate.

PREPARATION 6

To a mixture (210 ml) of pyridine and chlorosulfonic acid prepared in the same manner as described in Preparation 5 is added crosslinked cellulose (Cellulofine GCL-25, manufactured by Chisso Corp., Japan) (7.5 g), and the mixture is stirred at 65°-70° C. for 4 hours. After the reaction, the reaction mixture is cooled and then neutralized with aqueous sodium hydroxide. The gel thus obtained is separated by filtration and washed well with 0.01M phosphate buffered saline solution to give a crosslinked cellulose sulfate (7.2 g).

PREPARATION 7

To a mixture (210 ml) of pyridine and chlorosulfonic acid prepared in the same manner as described in Preparation 5 is added 30 ml of crosslinked agarose (Sepharose CL-6B, manufactured by Pharmacia, Sweden) containing pyridine, and the mixture is stirred at 65°-70° C. for 4 hours. After the reaction, the reaction mixture is cooled and then neutralized with aqueous sodium hydroxide. The gel thus obtained is separated by filtration and washed well with 0.01M phosphate buffered saline solution to give a crosslinked agarose sulfate (23 ml).

EXAMPLE 1

The Cellulofine GC-15 sulfate gel obtained in the same manner as in Preparation 1 is packed within a column (16 mmφ×100 mm), and this is equilibrated with 0.2M sodium chloride-added 0.01M phosphate buffer (pH 8.0, specific conductivity: about 17.5 ms/cm). A supernatant (specific conductivity: about 17.5 ms/cm, pH 8.0; 800 ml) of a fermenter culture of *B. pertussis* phase I Tohama strain is passed through the column. After washing well the column with the same buffer solution as above to remove contaminants, the adsorbed material is eluted with 1.5M sodium chloride-added phosphate buffer solution (pH 7.6) to give a fraction containing F-HA (30 ml).

The analytical data of the supernatant of culture, the fraction passed through, and the fraction containing purified F-HA are shown in Table 1.

The recovery rate of F-HA was 90%, the degree of purification (specific activity of the fraction of the purified F-HA/specific activity of the supernatant of culture) was 31 times. Besides, the LPF-HA activity of the fraction of the purified F-HA was less than 10 ELISA unit/ml [measured by Hapto-ELISA method, cf. Sato Y. et al., Symposium on Toxins, proceeding of the 28th Symposium on Toxins, 141-144 (1981)].

TABLE 1

| | Samples | | |
|---|---|---|---|
| Analytical items | Supernatant of culture (starting material) | Fraction passed through | Fraction of purified F-HA |
| Content of HA (F-HA-ELISA unit/ml) | 1,800 | 2 | 43,200 |
| Content of protein (mg/ml) (1) | 0.46 | 0.44 | 0.36 |
| Specific activity (2) | $3.9 \times 10^3$ | 4.5 | $1.2 \times 10^5$ |
| Pyrogen test in rabbit (Total in two | 4.2 | 4.2 | 0.6 |

TABLE 1-continued

| Analytical items | Samples: Supernatant of culture (starting material) | Fraction passed through | Fraction of purified F-HA |
|---|---|---|---|
| rabbits, °C.) (3) | | | |

[Notes]:
(1) It is shown as a protein content when calculated as protein nitrogen measured by Kjeldahl method × 6.25.
(2) It is shown in F-HA-ELISA unit/mg protein.
(3) It was done in accordance with the method described in Minimum Requirement of Biological Products, Ministry of Health and Welfare, Japan, #287, 1981, wherein the test sample was diluted until protein content of 6.25 μg/ml.

EXAMPLE 2

The Abicel sulfate gel obtained in the same manner as in Preparation 2 is packed within a column (12 mmφ×10 mm), and this is equilibrated with 0.14M sodium chloride-added 0.01M phosphate buffer (pH 8.0). A supernatant (specific conductivity: about 10 ms/cm, pH 8.0; 400 ml) of a fermenter culture of *B. pertussis* phase I Tohama strain is passed through the column. After washing well the column with the same buffer solution as above to remove contaminants, the adsorbed material is eluted with 1.5M sodium chloride-added phosphate buffer solution (pH 7.6) to give a fraction containing F-HA (30 ml).

The analytical data of the supernatant of culture, the fraction passed through, and the fraction containing purified F-HA are shown in Table 2.

The recovery rate of F-HA was 91%, the degree of purification was 11 times.

TABLE 2

| Analytical items | Samples: Supernatant of culture (starting material) | Fraction passed through | Fraction of purified F-HA |
|---|---|---|---|
| Content of HA (F-HA-ELISA unit/ml) | 2,600 | 5.0 | 31,500 |
| Content of protein (mg/ml) (1) | 0.32 | 0.29 | 0.35 |
| Specific activity (2) | $8.1 \times 10^3$ | $1.7 \times 10^1$ | $0.9 \times 10^5$ |
| Pyrogen test in rabbit (Total in two rabbits, °C.) (3) | 3.8 | 3.8 | 0.6 |

[Notes]:
The notes in (1), (2) and (3) are the same as those in Table 1.

EXAMPLE 3

The Cellulofine GH-25 sulfate gel obtained in the same manner as in Preparation 3 is packed within a column (16 mmφ×100 mm), and this is equilibrated with 0.2M sodium chloride-added 0.01M phosphate buffer (pH 8.0). A supernatant (specific conductivity: about 17.5 ms/cm, pH 8.0; 800 ml) of a fermenter culture of *B. pertussis* phase I Tohama strain is passed through the column. After washing well the column with the same buffer solution as above to remove contaminants, the adsorbed material is eluted with 1.5M sodium chloride-added phosphate buffer solution (pH 7.6) to give a fraction containing F-HA (30 ml).

The analytical data of the supernatant of culture, the fraction passed through, and the fraction containing purified F-HA are shown in Table 3.

The recovery rate of F-HA was 94%, the degree of purification was 30 times.

According to the method as described in Minimum Requirement of Biological Products, "Pertussis Vaccine" (cf. Notification of the Pharmaceutical Affairs Bureau, Ministry of Health and Welfare, Japan, #287, 1981), the purified product was subjected to test for mouse body weight-decreasing toxicity, test for mouse leucocyte-increasing toxicity, test for freedom from heat-labile toxin, and test for mouse histamine sensitizing toxicity. As a result, in all tests, the purified product was the same as the control (a physiological saline solution was used), which means that no side effect was observed.

TABLE 3

| Analytical items | Samples: Supernatant of culture (starting material) | Fraction passed through | Fraction of purified F-HA |
|---|---|---|---|
| Content of HA (F-HA-ELISA unit/ml) | 1,970 | 3.0 | 49,400 |
| Content of protein (mg/ml) (1) | 0.46 | 0.44 | 0.38 |
| Specific activity (2) | $4.3 \times 10^3$ | 6.7 | $1.3 \times 10^5$ |
| Pyrogen test in rabbit (Total in two rabbits, °C.) (3) | 4.2 | 4.2 | 0.7 |

[Notes]:
The notes in (1), (2) and (3) are the same as those in Table 1.

EXAMPLE 4

The dextran sulfate agarose gel obtained in the same manner as in Preparation 4 is packed within a column (16 mmφ×100 mm), and this is equilibrated with 0.2M sodium chloride-added 0.01M phosphate buffer (pH 8.0, specific conductivity: about 17.5 ms/cm). A supernatant (specific conductivity: about 17.5 ms/cm, pH 8.0; 800 ml) of a fermenter culture of *B. pertussis* phase I Tohama strain is passed through the column. After washing well the column with the same buffer solution as above and further 0.20M sodium chloride-added phosphate buffer (pH 8.0, specific conductivity: about 17.5 ms/cm) to remove contaminants, the adsorbed material is eluted with 1.5M sodium chloride-added phosphate buffer solution (pH 7.8, specific conductivity: about 120 ms/cm) to give a fraction containing F-HA (29 ml).

The analytical data of the supernatant of culture, the fraction passed through, and the fraction containing purified F-HA are shown in Table 4.

The recovery rate of F-HA was 91%, the degree of purification was 13 times. Besides, the LPF-HA activity of the fraction of the purified F-HA was less than 10 Hp.-ELISA unit/ml [measured by Hapto-ELISA method, cf. Sato Y. et al., Symposium on Toxins, proceeding of the 28th Symposium on Toxins, 141–144 (1981)].

TABLE 4

| Analytical items | Samples: Supernatant of culture (starting material) | Fraction passed through | Fraction of purified F-HA |
|---|---|---|---|
| Content of HA (F-HA-ELISA unit/ml) | 1,800 | 0 | 45,000 |
| Content of protein (mg/ml) (1) | 0.25 | 0.20 | 0.5 |
| Specific activity (2) | $7.2 \times 10^3$ | 0 | $0.9 \times 10^5$ |
| Pyrogen test in rabbit (Total in two | 3.7 | 3.5 | 0.6 |

TABLE 4-continued

| Analytical items | Samples | | |
|---|---|---|---|
| | Supernatant of culture (starting material) | Fraction passed through | Fraction of purified F-HA |
| rabbits, °C.) (3) | | | |

[Notes]:
The notes in (1), (2) and (3) are the same as those in Table 1.

EXAMPLE 5

The dextran sulfate-agarose gel (200 ml) obtained in the same manner as in Preparation 4 is immerged in 0.2M sodium chloride-added 0.01M phosphate buffer (pH 8.0), and it is equilibrated by repeated decantation. The gel is added to a supernatant (specific conductivity: about 17.5 ms/cm, pH 8.0, 8 liters) of the same fermenter culture of *B. pertussis* phase I Tohama strain as used in Example 4, and the mixture is stirred at 4° C. for about 2 hours. The mixture is filtered with a glass filter (70 mmφ×150) to separate the gel. The gel on the glass filter is washed by pouring thereon 0.20M sodium chloride-added phosphate buffer (pH 8.0), followed by gentle suction. Then, 1.5M sodium chloride-added phosphate buffer (pH 7.8, 300 ml) is poured to the gel, and the mixture is gently stirred for about 15 minutes, followed by suction to give purified F-HA fraction (300 ml).

The analytical data of the supernatant of culture, the fraction passed through, and the fraction containing purified F-HA are shown in Table 5.

The recovery rate of F-HA was 83%, the degree of purification was 19 times.

TABLE 5

| Analytical items | Samples | | |
|---|---|---|---|
| | Supernatant of culture (starting material) | Fraction passed through | Fraction of purified F-HA |
| Content of HA (F-HA-ELISA unit/ml) | 1,800 | 0 | 40,000 |
| Content of protein (mg/ml) (1) | 0.25 | 0.23 | 0.28 |
| Specific activity (2) | $7.2 \times 10^3$ | 0 | $1.4 \times 10^5$ |
| Pyrogen test in rabbit (Total in two rabbits, °C.) (3) | 3.7 | 3.7 | 0.6 |

[Notes]:
The notes in (1), (2) and (3) are the same as those in Table 1.

EXAMPLE 6

The dextran sulfate-Sepharose CL 4B gel (manufactured by Pharmacia, Sweden) is packed within a column (50 mmφ×100 mm), and this is equilibrated with 0.2M sodium chloride-added 0.01M phosphate buffer (pH 8.0). A supernatant (specific conductivity: about 17.5 ms/cm, pH 8.0; 8 liters) of a fermenter culture of *B. pertussis* phase I Tohama strain is passed through the column. After washing well the column with the same buffer solution as above to remove contaminants, the adsorbed material is eluted with 1.5M sodium chloride-added phosphate buffer solution (pH 7.6) to give a fraction containing F-HA (580 ml).

The analytical data of the supernatant of culture, the fraction passed through, and the fraction containing purified F-HA are shown in Table 6.

The recovery rate of F-HA was 93%, the degree of purification was about 50 times.

According to the method as described in Minimum Requirement of Biological Products, "Pertussis Vaccine" (cf. Notification of the Pharmaceutical Affairs Bureau, Ministry of Health and Welfare, Japan, #287, 1981), the purified product was subjected to test for mouse body weight-decreasing toxicity, test for mouse leucocyte-increasing toxicity, test for freedom from heat-labile toxin, and test for mouse histamine sensitizing toxicity. As a result, in all tests, the purified product was the same as the control (a physiological saline solution was used), which means that no side effect was observed.

TABLE 6

| Analytical items | Samples | | |
|---|---|---|---|
| | Supernatant of culture (starting material) | Fraction passed through | Fraction of purified F-HA |
| Content of HA (F-HA-ELISA unit/ml) | 1,120 | 0 | 14,300 |
| Content of protein (mg/ml) (1) | 0.51 | 0.42 | 0.13 |
| Specific activity (2) | $2.2 \times 10^3$ | 0 | $1.1 \times 10^5$ |
| Pyrogen test in rabbit (Total in two rabbits, °C.) (3) | 4.0 | 4.1 | 0.4 |

[Notes]:
The notes in (1), (2) and (3) are the same as those in Table 1.

EXAMPLE 7

The Sephadex G-50 sulfate gel obtained in the same manner as in Preparation 5 is packed within a column (16 mmφ×100 mm), and this is equilibrated with 0.2M sodium chloride-added 0.01M phosphate buffer (pH 8.0, specific conductivity: about 17.5 ms/cm). A supernatant (specific conductivity: about 17.5 ms/cm, pH 7.6; 800 ml) of a fermenter culture of *B. pertussis* phase I Tohama strain is passed through the column. After washing well the column with the same buffer solution as above to remove contaminants, the adsorbed material is eluted with 1.5M sodium chloride-added phosphate buffer solution (pH 7.6) to give a fraction containing F-HA (30 ml).

The analytical data of the supernatant of culture, the fraction passed through, and the fraction containing purified F-HA are shown in Table 7.

The recovery rate of F-HA was 94%, the degree of purification was about 35 times. Besides, the LPF-HA activity of the fraction of the purified F-HA was less than 10 Hp.-ELISA unit/ml.

TABLE 7

| Analytical items | Samples | | |
|---|---|---|---|
| | Supernatant of culture (starting material) | Fraction passed through | Fraction of purified F-HA |
| Content of HA (F-HA-ELISA unit/ml) | 2,000 | 0 | 50,000 |
| Content of protein (mg/ml) (1) | 0.46 | 0.44 | 0.34 |
| Specific activity (2) | $4.3 \times 10^3$ | 0 | $1.5 \times 10^5$ |
| Pyrogen test in rabbit (Total in two rabbits, °C.) (3) | 4.2 | 4.2 | 0.6 |

[Notes]:
The notes in (1), (2) and (3) are the same as those in Table 1.

EXAMPLE 8

The Cellulofine GCL-25 sulfate gel obtained in Preparation 6 is packed within a column (16 mmϕ×100 mm), and this is equilibrated with 0.14M sodium chloride-added 0.01M phosphate buffer (pH 8.0). A supernatant (specific conductivity: about 10 ms/cm, pH 8.0; 800 ml) of the same rot of a fermenter culture of *B. pertussis* phase I Tohama strain as used in Example 7 is passed through the column. After washing well the column with the same buffer solution as above to remove contaminants, the adsorbed material is eluted with 1.5M sodium chloride-added phosphate buffer solution (pH 7.6) to give a fraction containing F-HA (30 ml).

The analytical data of the supernatant of culture, the fraction passed through, and the fraction containing purified F-HA are shown in Table 8.

The recovery rate of F-HA was 87%, the degree of purification was 26 times.

TABLE 8

| | Samples | | |
|---|---|---|---|
| Analytical items | Supernatant of culture (starting material) | Fraction passed through | Fraction of purified F-HA |
| Content of HA (F-HA-ELISA unit/ml) | 1,950 | 2 | 45,000 |
| Content of protein (mg/ml) (1) | 0.46 | 0.44 | 0.40 |
| Specific activity (2) | $4.2 \times 10^3$ | 4.5 | $1.1 \times 10^5$ |
| Pyrogen test in rabbit (Total in two rabbits, °C.) (3) | 4.2 | 4.2 | 0.8 |

[Notes]:
The notes in (1), (2) and (3) are the same as those in Table 1.

EXAMPLE 9

The Sepharose CL-6B sulfate gel obtained in the same manner as in Preparation 7 is packed within a column (16 mmϕ×100 mm), and this is equilibrated with 0.2M sodium chloride-added 0.01M phosphate buffer (pH 8.0). A supernatant (specific conductivity: about 17.5 ms/cm, pH 8.0; 800 ml) of the same lot of a fermenter culture of *B. pertussis* phase I Tohama strain as used in Example 7 is passed through the column. After washing well the column with the same buffer solution as above to remove contaminants, the adsorbed material is eluted with 1.5M sodium chloride-added phosphate buffer solution (pH 7.6) to give a fraction containing F-HA (28 ml).

The analytical data of the supernatant of culture, the fraction passed through, and the fraction containing purified F-HA are shown in Table 9.

The recovery rate of F-HA was 84%, the degree of purification was 33 times. Besides, the LPF-HA activity was less than 10 Hp.-ELISA unit/ml.

According to the method as described in Minimum Requirement of Biological Products, "Pertussis Vaccine" (cf. Notification of the Pharmaceutical Affairs Bureau, Ministry of Health and Welfare, Japan, #287, 1981), the purified product was subjected to test for mouse body weight-decreasing toxicity, test for mouse leucocyte-increasing toxicity, test for freedom from heat-labile toxin, and test for mouse histamine sensitizing toxicity. As a result, in all tests, the purified product was the same as the control (a physiological saline solution was used), which means that no side effect was observed.

TABLE 9

| | Samples | | |
|---|---|---|---|
| Analytical time | Supernatant of culture (starting material) | Fraction passed through | Fraction of purified F-HA |
| Content of HA (F-HA-ELISA unit/ml) | 2,000 | 5 | 48,000 |
| Content of protein (mg/ml) (1) | 0.46 | 0.42 | 0.35 |
| Specific activity (2) | $4.3 \times 10^3$ | $1.2 \times 10^1$ | $1.4 \times 10^5$ |
| Pyrogen test in rabbit (Total in two rabbits, °C.) (3) | 4.2 | 4.2 | 0.6 |

[Notes]:
The notes in (1), (2) and (3) are the same as those in Table 1.

What is claimed is:

1. A method for the purification of Filamentous Hemagglutinin (F-HA) produced by a microorganism of the genus Bordetella, which comprises contacting an F-HA-containing solution with a gel selected from the group consisting of a cellulose sulfate gel, a polysaccharide gel chemically bound with dextran sulfate and a crosslinked polysaccharide sulfate gel to adsorb the F-HA and eluting the adsorbed F-HA from the gel.

2. The method according to claim 1, wherein the gel selected from a cellulose sulfate gel, a polysaccharide gel chemically bound with dextran sulfate and a crosslinked polysaccharide sulfate gel is previously equilibrated by treating it with a buffer having a pH of 6.9 to 9.0 and a specific conductivity of 5.0 to 25.0 ms/cm and then subjected to the adsorption of F-HA.

3. The method according to claim 1, wherein the adsorption is carried out under the conditions of a pH of 6.0 to 8.0, a temperature of 0° to 30° C. and a specific conductivity of 5.0 to 25.0 ms/cm.

4. The method according to claim 1, wherein the elution of F-HA from the gel is carried out with a buffer having a pH of 5.0 to 10.0 and a specific conductivity of 25.0 to 130 ms/cm.

5. The method according to claim 4, wherein the F-HA-adsorbed gel is washed with a buffer having a pH of 5.0 to 10.0 and a specific conductivity of 5.0 to 25.0 ms/cm before the elution.

6. The method according to claim 1, wherein the starting F-HA-containing solution is a culture supernatant of *Bordetella pertussis.*

7. The method according to claim 1, wherein the cellulose sulfate is a sulfuric acid ester of a cellulose selected from a crystalline cellulose and a cellulose having crystalline area and non-crystalline area.

8. The method according to claim 1, wherein the polysaccharide gel chemically bound with dextran sulfate is a dextran sulfate-agarose gel, a dextran sulfate-dextran gel, and a dextran sulfate-cellulose gel.

9. The method according to claim 1, wherein the crosslinked polysaccharide sulfate is a member selected from the group consisting of a crosslinked dextran sulfate, a crosslinked agarose sulfate, and a crosslinked cellulose sulfate.

10. The method according to claim 9, wherein the crosslinked dextran sulfate is an epichlorohydrin-crosslinked dextran sulfate.

11. The method according to claim 9, wherein the crosslinked agarose sulfate is an epichlorohydrin-crosslinked agarose sulfate.

12. The method according to claim 8, wherein the crosslinked cellulose sulfate is an epichlorohydrin-crosslinked cellulose sulfate.

* * * * *